United States Patent
Main et al.

(10) Patent No.: US 10,228,302 B2
(45) Date of Patent: Mar. 12, 2019

(54) APPARATUS FOR TESTING MOORING BOLLARD HAVING A PULLING DEVICE AND A PULLING FORCE MEASURING DEVICE

(71) Applicant: TYNE & WEAR MARINE LIMITED, Tyne and Wear (GB)

(72) Inventors: Jeffrey Alexander Main, Tyne and Wear (GB); John Robert Cramman, Tyne and Wear (GB)

(73) Assignee: BOLLARD LOAD TESTING LIMITED (GB)

( * ) Notice: Subject to any disclaimer, the term of this patent is extended or adjusted under 35 U.S.C. 154(b) by 71 days.

(21) Appl. No.: 15/115,516

(22) PCT Filed: Feb. 2, 2015

(86) PCT No.: PCT/GB2015/050274
§ 371 (c)(1),
(2) Date: Jul. 29, 2016

(87) PCT Pub. No.: WO2015/114380
PCT Pub. Date: Aug. 6, 2015

(65) Prior Publication Data
US 2017/0176284 A1 Jun. 22, 2017

(30) Foreign Application Priority Data

Jan. 31, 2014 (GB) .................................. 1401684.4

(51) Int. Cl.
*G01M 5/00* (2006.01)
*E02B 3/24* (2006.01)
(Continued)

(52) U.S. Cl.
CPC ............. *G01M 5/005* (2013.01); *B63B 21/06* (2013.01); *G01M 5/0075* (2013.01); *G01N 3/08* (2013.01);
(Continued)

(58) Field of Classification Search
CPC ............. G01M 5/0025; G01M 5/0066; G01M 5/0075; G01M 7/08; G01M 5/007;
(Continued)

(56) References Cited

U.S. PATENT DOCUMENTS 5,447,114 A * 9/1995 Korsgaard ............ B63B 22/023
114/230.13
5,723,794 A * 3/1998 Discenzo ................ G01L 1/241
73/800

(Continued)

FOREIGN PATENT DOCUMENTS

CN 103175645 6/2013
CN 203132753 8/2013
(Continued)

OTHER PUBLICATIONS

"Field Testing of Floating Modular Hybrid Pier Completed by UCSD Structural Engineers", Internet Citation, 2007, pp. 1-12, XP002632654, Retrieved from the Internet: URL: http://structures.ucsd.edu/node/1592 , retrieved Apr. 13, 2011.
(Continued)

*Primary Examiner* — Hardshad R Patel
*Assistant Examiner* — Brandi N Hopkins
(74) *Attorney, Agent, or Firm* — The Belles Group, P.C.

(57) ABSTRACT

An apparatus for testing a mooring bollard is disclosed. The apparatus has first and second connector ropes for attaching the apparatus to a pair of bollards. There is also a pulling device (such as a hydraulic ram) for applying a pulling force to the bollards via the connector ropes. The device further
(Continued)

includes a pulling force measuring device connected between the ram and one of the connector ropes, for measuring the pulling force being applied between the bollards. Finally there is a computer system for controlling the hydraulic ram and for gathering data from the data measuring device.

20 Claims, 4 Drawing Sheets

(51) Int. Cl.
*B63B 21/06* (2006.01)
*G01N 3/08* (2006.01)

(52) U.S. Cl.
CPC ........ *E02B 3/24* (2013.01); *G01N 2203/0017* (2013.01); *G01N 2203/0647* (2013.01); *G01N 2203/0658* (2013.01)

(58) Field of Classification Search
CPC .. G01N 29/045; G01N 29/38; G01N 29/4427; G01N 29/46; G01N 2291/0232; G01N 2291/0234; G01N 19/00; G01N 3/08; B63B 21/00; G01L 5/103; G01L 5/102; G01L 5/107
See application file for complete search history.

(56) References Cited

U.S. PATENT DOCUMENTS

| | | | | |
|---|---|---|---|---|
| 9,315,239 | B2 * | 4/2016 | Gill | B63B 21/20 |
| 2014/0017013 | A1 * | 1/2014 | Ma | B63B 21/20 |
| | | | | 405/195.1 |
| 2014/0026796 | A1 * | 1/2014 | Leverette | B63B 21/00 |
| | | | | 114/230.24 |
| 2014/0338581 | A1 * | 11/2014 | Gill | B63B 21/04 |
| | | | | 114/230.21 |

FOREIGN PATENT DOCUMENTS

| | | |
|---|---|---|
| DE | 102011100370 | 11/2012 |
| GB | 2502993 | 12/2013 |
| JP | S59199389 | 11/1984 |
| JP | S62263441 | 11/1987 |
| SU | 431058 | 6/1974 |

OTHER PUBLICATIONS

Corresponding International Search Report and Written Opinion for PCT/GB2015/050274 dated Apr. 23, 2015.
Corresponding UKIOP Search Report dated Jul. 14, 2014.

* cited by examiner

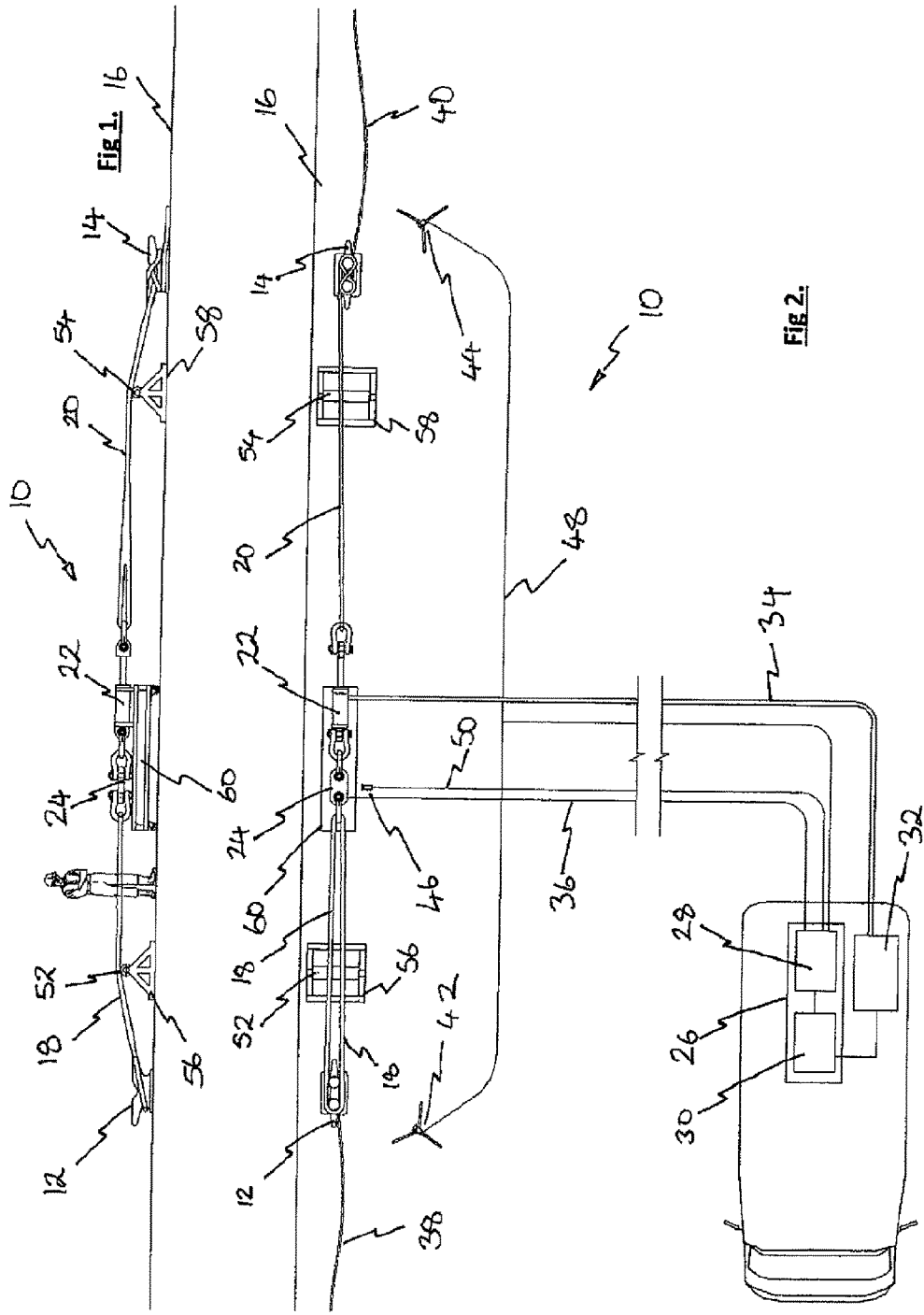

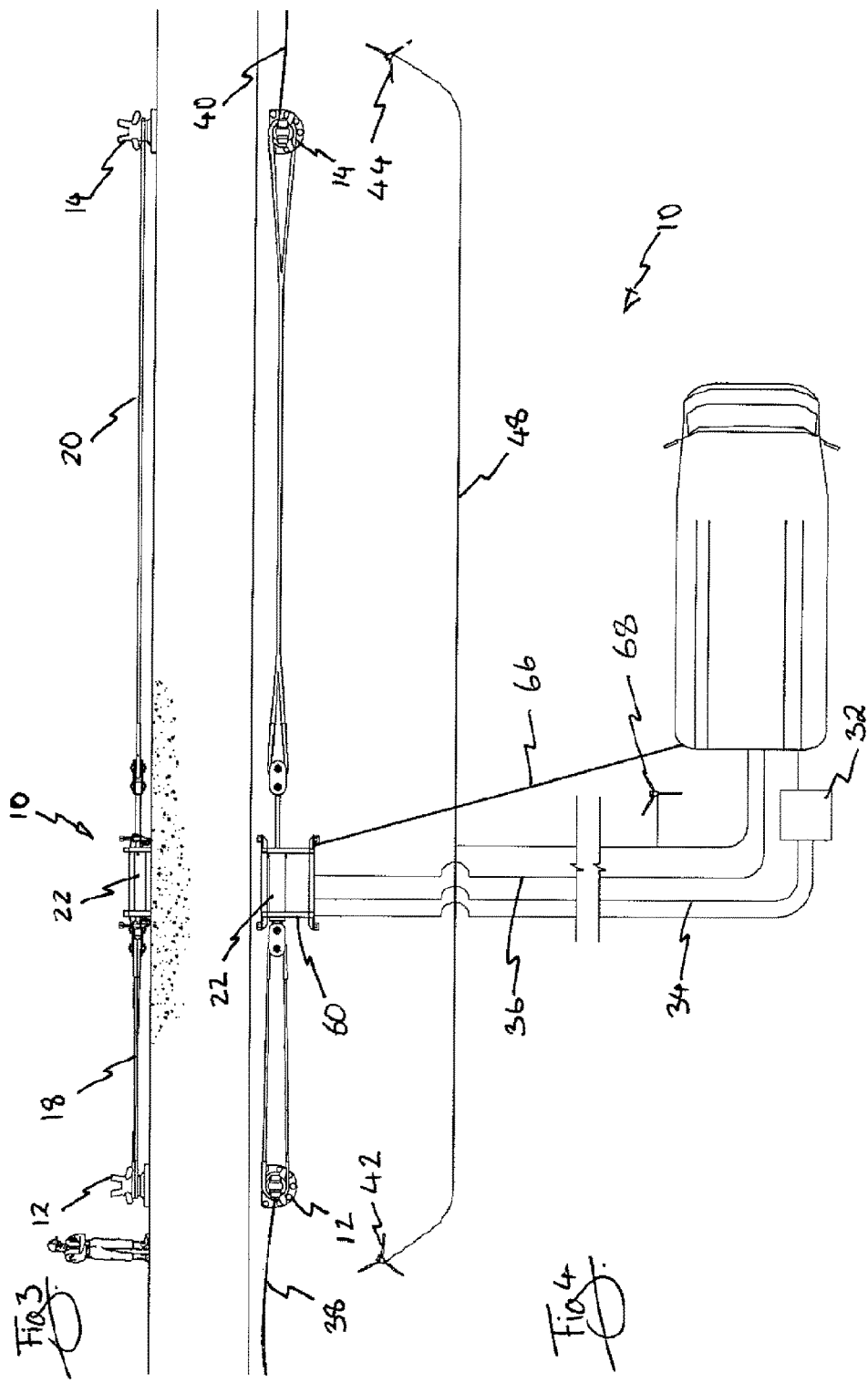

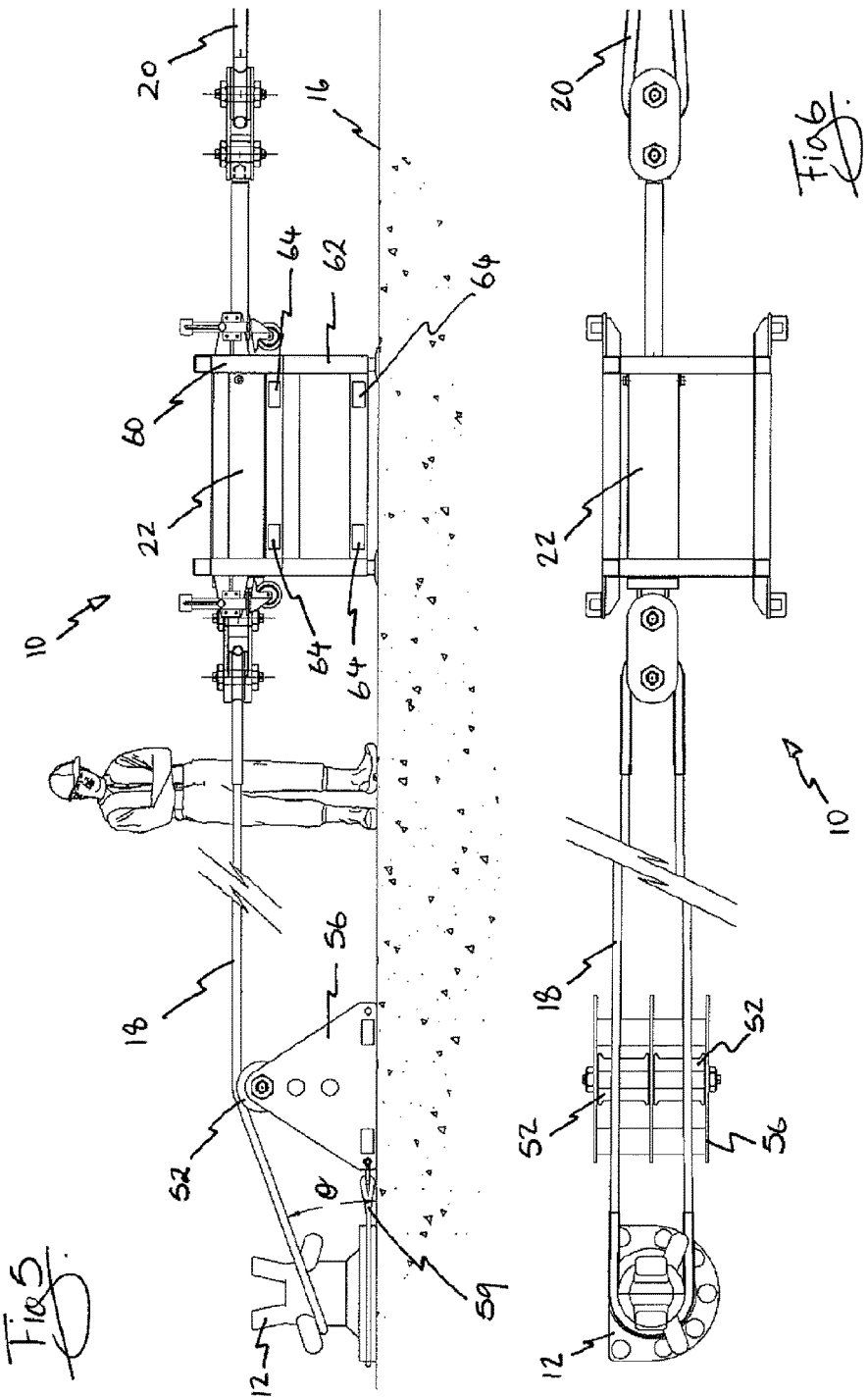

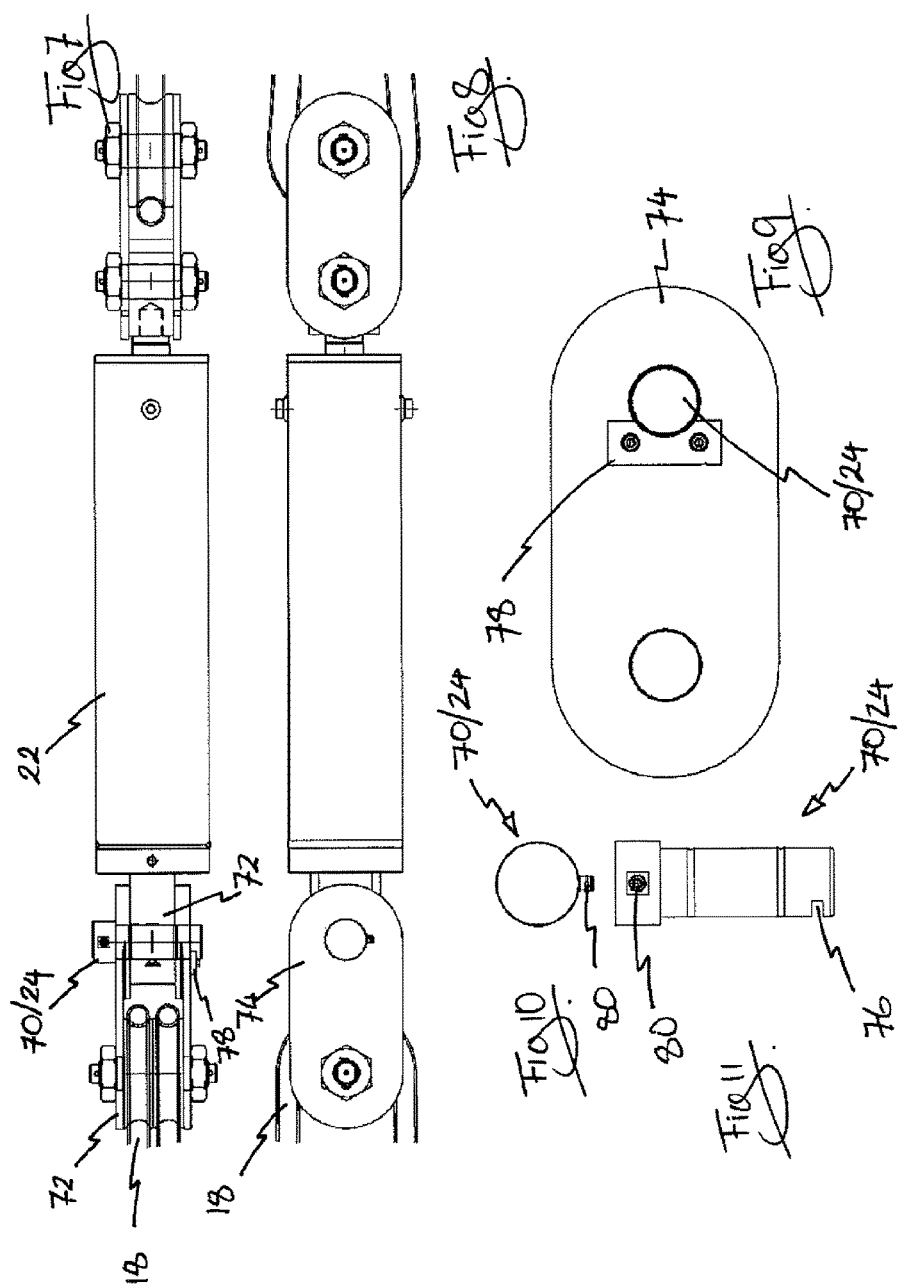

APPARATUS FOR TESTING MOORING BOLLARD HAVING A PULLING DEVICE AND A PULLING FORCE MEASURING DEVICE

CROSS-REFERENCE TO RELATED PATENT APPLICATIONS

The present application is a U.S. national stage application under 35 U.S.C. § 371 of PCT Application No. PCT/GB2015/050274, filed Feb. 2, 2015, which in turn claims priority to GB Application No. 1401684.4, filed Jan. 31, 2014, the entireties of which are incorporated herein by reference.

The present invention relates to a bollard testing system and relates particularly, but not exclusively, to an apparatus and a method for safety testing a quayside bollard or other ship mooring at a port, harbour or shipyard.

The use of mooring bollards to tie up waterborne vessels is a centuries-old technique. In recent years the size of seafaring ships has increased significantly and such vessels require significant amounts of space in a port in order to moor. Increasingly large ships are subject to large forces resulting from wind and wave action acting against them when they are docked in a port. A large ship typically uses several mooring lines and several bollards in order to tie up. However, the force is applied to the bollard can be significant when a strong wind blows against the side of a ship with a tall side face.

In adverse weather conditions it is not uncommon for tugboats to be used to apply a constant pushing force to one side of a large ship where a very strong wind is blowing against the other side of the vessel.

A bollard that is damaged, or that has its fixing to the quayside damaged, represents a significant danger if a large pulling force is applied to it by a moored ship. A method of testing the strength of a bollard is to tie a rope around the bollard and attach the rope to a tugboat which then applies a pulling force to the bollard. In the event that the tugboat is able to pull the bollard from its fixings the boat, and the people thereon, are in significant danger from the bollard.

Preferred embodiments of the present invention seek to overcome the above described disadvantages of the prior art.

According to an aspect of the present invention there is provided an apparatus for testing a mooring bollard, the apparatus comprising:
a first connector for attaching the apparatus to a first bollard;
a second connector for attaching the apparatus to a second bollard;
at least one pulling device for applying a pulling force to said first and second bollards via said first and second connectors, said pulling device under the control of at least one controller; and
at least one pulling force measuring device connected between said pulling device and one of said first and second connectors, for measuring the pulling force being applied between the first and second bollards, wherein data from said measuring device is recorded on at least one data logging device.

By providing an apparatus that connects two bollards, via first and second connectors with a pulling device and force measuring device, the advantage is provided that the strength of the bollards and their fixings can be tested. Furthermore, by applying such a test to a pair of bollards, that is applying a predetermined pulling force between the bollards, it can be determined that both of these bollards are capable of maintaining a vessel in position whilst being pulled at that predetermined force. This test can be easily applied without putting the testing personnel in direct danger resulting from any movement of the bollards if they are insufficiently fixed to the ground.

The apparatus may further comprise at least one connector lifter for engaging at least one said connector causing it to extend from its attachment to one of said first and second bollards at an angle not parallel to a line connecting said first and second bollards.

By providing a connector lifter the advantage is provided that the angle at which the connector extends from the bollard is not horizontal. As a result, non-horizontal components are added to the force applied to the bollard ensuring that faults in the bollard, or its connection to the quayside, which do not affect horizontal movement, are also identified by the test. Furthermore, the connector lifter allows the connector to be attached to the bollard and be pulled at an angle more closely resembling the angle at which a mooring line from a ship is tied to a bollard.

In a preferred embodiment the connector lifter comprises at least one roller for supporting said connector.

The apparatus may further comprise acoustic emission testing means for positioning on or adjacent the bollard for detecting acoustic emissions during a test.

By providing acoustic emission testing means the advantage is provided that sounds produced during the application of force to the bollard can be detected and if necessary the test terminated before damage to the bollard occurs. In particular, the processor is able to distinguish sounds which are known to be normal during a test and not indicative of damage to the bollard, sounds that are known to be indicative of damage to the bollard and sounds which are not recognised. For example, a normal sound not indicative of damage could result from movement of the rope and should not result in the test being terminated. A sound that is indicative of cracking concrete adjacent the bollard would be known to be indicative of damage and should result in the termination of the test. An example of an unknown sound might result from ground works being undertaken somewhere nearby the test site. As a result, the processor could reduce the rate of increase of force on the bollard as a precaution.

The apparatus may also further comprise sound creation means for positioning on or adjacent the bollard for creating acoustic resonance within the material forming and adjacent the bollard.

By including sound creation means the acoustic resonance within and adjacent the bollard can be tested to identify changes in the acoustic resonance during the test which indicate the early stages of damage occurring thereby allowing the test to be terminated before any further damage occurs. The use of acoustic resonance is more sensitive to change than acoustic emission as it does not rely on the damage being sufficient to produce a sound emission.

In a preferred embodiment at least one of said first and second connectors comprise ropes.

In another preferred embodiment the ropes comprise ultrahigh molecular weight polyethylene.

By using ultrahigh molecular weight polyethylene ropes the advantage is provided that a rope that is sufficiently strong to apply the required by force to the bollards is provided whilst remaining a lightweight and easy to handle connector. Furthermore, ultrahigh molecular weight polyethylene is a very low stretching coefficient and therefore does not stretch during the test which would require a longer draw on a hydraulic ram used in the test. This low stretching coefficient also results in an almost zero elastic pull on the rope which in turn increases the safety in the operation of the apparatus. This is particularly because, in the event that a pull test results in damage to a bollard for example where a bollard is pulled free of the quayside, it will not be launched by the elastic tension of the rope since none is present. Instead, the bollard will simply move slightly towards the hydraulic ram.

In a preferred embodiment the pulling device comprises at least one hydraulic ram.

In another preferred embodiment the pulling force measuring device comprises at least one load cell.

The apparatus may further comprise at least one processor for processing said data and providing signals to said controller in response to said data.

The apparatus may also further comprise safety connectors attached to said connectors and for attached to further bollards.

By providing safety connectors, also referred to as taglines or tethers, the advantage is provided that in the event that one or other of the bollards fails during the test, the safety connector will limit the movement of the bollard, thereby significantly reducing the risk to objects or people in the vicinity of the bollard.

The apparatus may further comprise at least one image data capturing device for capturing image data relating to the apparatus.

In a preferred embodiment the image data capturing device is connected to said controller such that said controller controls power to said pulling device in response to said image data indicating a movement exceeding a predetermined level.

By providing image data capturing devices that are monitoring the bollards and connecting them to the controller, the advantage is provided that a high-speed shutdown of the apparatus can be provided. As a result, any damage that the apparatus may be causing to a bollard can be limited. This may allow the bollard to be repaired rather than resulting in excess damage of the bollard requiring it necessarily to be replaced. Furthermore, the high-speed shutdown of the apparatus provides additional safety for objects or people in the vicinity of the bollard.

According to another aspect of the present invention there is provided a method of testing a mooring bollard, comprising the steps:

attaching a first connector to a first bollard;

attaching a second connector to a second bollard, wherein the first and second connectors are connected to at least one pulling device for applying a pulling force to said first and second bollards via said first and second connectors under the control of at least one controller, and at least one pulling force measuring device connected between said pulling device and one of said first and second connectors, for measuring the pulling force being applied between the first and second bollards; and using said controller to cause said pulling device to apply said pulling force to said first and second bollards via said first and second connectors and recording said data from said measuring device on at least one data logging device.

The method may further comprise locating at least one connector lifter between the bollard and said pulling device, the connector lifter for engaging at least one said connector causing it to extend from its attachment to one of said first and second bollards at an angle not parallel to a line connecting said first and second bollards.

The method may also further comprise locating acoustic emission testing means, for detecting acoustic emissions during said test, on or adjacent the bollard.

In a preferred embodiment the method further comprises locating sound creation means, for creating acoustic resonance within the material forming and adjacent the bollard, on or adjacent the bollard.

The method may further comprise using at least one processor to process said data and provide signals to said controller in response to said data.

The method may also further comprise connecting at least one image data capturing device to said controller such that said controller controls power to said pulling device in response to said image data indicating a movement exceeding a predetermined level.

The method may further comprise further comprising analysing said data and determining whether said data indicates a pass or fail.

In a preferred embodiment the analysis is undertaken using a computing device remote from a location where said test is being conducted.

Preferred embodiments of the present invention will now be described, by way of example only, and not in any limitative sense, with reference to the accompanying drawings in which:

FIG. 1 is a side view of the apparatus of the present invention;

FIG. 2 is a plan view of the apparatus of FIG. 1;

FIG. 3 is a side view of an alternative apparatus of the present invention;

FIG. 4 is a plan view of the apparatus of FIG. 3;

FIG. 5 is a close up view of the apparatus of FIGS. 3 and 4 with some additional features;

FIG. 6 is a plan view of the apparatus of FIG. 5;

FIGS. 7 and 8 are close up side and plan views of a portion of the apparatus of FIG. 5;

FIG. 9 is a further close-up plan view of a portion of the apparatus shown in FIG. 8; and FIGS. 10 and 11 are plan and side views of a pin used in the apparatus of FIGS. 3 to 9.

Referring to the figures, an apparatus 10 is provided to test mooring bollards 12 and 14. The apparatus 10 in particular tests the force that can be applied between the bollards 12 and 14 to determine the strength of their connection to the ground of quayside 16.

The apparatus includes a first connector, in the form of first rope 18, for attaching the apparatus 10 to the first bollard 12. The apparatus also has a second connector, in the form of second rope 20, for attaching the apparatus 10 to second bollard 14.

Located between first and second ropes 18 and 20 are a pulling device, in the form of hydraulic ram 22, and a pulling force measuring device, in the form of load cell 24. The hydraulic ram 22 applies a pulling force to the first and second bollards 12 and 14 via the first and second ropes 18 and 20. In one embodiment the ram 22 is capable of applying a pulling force up to 120 tonnes and all other components are designed to be of sufficient strength to operate comfortably to this force and beyond. Depending upon the circumstances the required pulling force may be more or less than this suggested maximum force.

The hydraulic ram 22 acts under the control of a controller, in the form of processor 26, which has a data receiving portion 28 and a controller portion 30 which controls a hydraulic power pack 32 which in turn powers hydraulic ram 22 by passing hydraulic fluid through hydraulic hose 34. The load cell 24 is located between the hydraulic ram 22 and first rope 18 and measures the pulling force applied between bollards 12 and 14. Data from load cell 24 is sent to data receiving portion 28 of processor 26 via data cable 36.

The first and second ropes 18 and 20 are preferably formed from an ultrahigh molecular weight polyethylene. However, it should be noted that any rope of sufficient strength can be used and indeed these connectors need not be rope and could be any other suitable form of connector such as a chain or steel cable. However, ultrahigh molecular weight polyethylene ropes are lightweight and easy to handle making them particularly advantageous to use in this product. Two further ropes, referred to as tethers or taglines 38 and 40, are preferably also attached to bollards 12 and 14 respectively. These taglines 38 and 40 act as a safety device in the event that the apparatus 10 is able to pull with sufficient force to dislodge either of the bollards 12 and 14. In order to act as a safety line, the taglines 38 and 40 must be attached to some other substantially immovable object and this may for example be further bollards, not shown in these figures.

Apparatus 10 preferably further comprises image data capture devices in the form of cameras 42, 44 and 46. Cameras 42 and 44 are located so as to gather images of bollards 12 and 14. This image data is sent via data cable 48 to data receiving portion 28 of processor 26. Similarly camera 46 sends data via data cable 50.

The apparatus 10 preferably also further includes at least one connector lifter in the form of a pair of rollers 52 and 54 that are located on roller stands 56 and 58. The rollers 52 and 54 and stands 56 and 58 cause the angle of attachment of the rope 18 to move away from the horizontal (as seen in FIG. 3) and approach an angle which is more representative of the angle at which a mooring rope would extend from a ship to the bollard. This is illustrated in FIG. 1 and in particular in FIG. 5 in which a roller 52 and stand 56 are positioned so that the rope attaches to the bollard at an angle θ. In the example shown in FIG. 5 the angle θ is selected and 20°. It is particularly important that the use of the rollers and stands are included as part of the test procedure in order to ensure that there is at least some upward component to the pulling force that is being applied to the bollard 12 being tested. The configuration shown in FIGS. 3 and 4 provides an important element of the testing process but could miss certain faults and does not realistically represent the action of a moored ship on a bollard. The stands 56 and 58 are provided with a tether line 59 which extends around the bollards 12 preventing the stand 56 from moving relative to the bollards and thereby maintaining the angle θ. An alternative to the combination of rollers and stands would be to provide stands with a surface, such as a tubular surface, over which the ropes are able to slide.

There is also provided a trolley 60 on which the hydraulic ram 22 and load cell 24 are located. These rollers and their stands, together with the trolley, assist in ensuring the free movement of the ropes 18 and 20 to ensure that the force being applied by hydraulic ram 22 is evenly distributed between the pair of bollards 12 and 14. In the example shown in FIG. 5 an additional raising platform component 62 is used to lift the trolley 60 so that the hydraulic ram 22 is positioned at the same height as rollers 52 and 54. Therefore the portions of the ropes 18 and 20 between the rollers 52 and the ram 22 are substantially horizontal. In the embodiment shown in FIG. 5 both the trolley 60 and platform 62 have forklift truck tine apertures 64 which allow the trolley and platform to be manoeuvred using a forklift truck.

In the embodiment of FIG. 4, a couple of additional components are shown including a tether 66 and an additional camera 68. The tether 66 is used to connect the apparatus, and in particular the trolley 60, to the vehicle. In the event that the trolley 60 should fall over the quayside the tether 66 will prevent the apparatus from being lost in the often deep water of the port. The tether 66 can be attached to any suitable object that is sufficiently immovable to bear the weight of the trolley and other parts of the apparatus, including for example a forklift truck or a clamp attached to the railway track type rails which commonly run along quaysides. The additional camera is used to capture an overall view of the operation.

With particular reference to FIGS. 7 to 11, a further difference between the apparatus shown in FIGS. 3 to 6 from that shown in FIGS. 1 and 2, is the relocation of the load cell 24 into a pin 70. The pin 70 is used to connect an end connector 72 of ram 22 to a shackle 74 onto which the rope 18 is (or in the example shown in FIG. 7 ropes 18 are) connected. The load cell 24 has been relocated into the pin 70 in order to facilitate easy interchange of the load cells. In order to ensure that the apparatus is operating correctly and giving accurate measurement of the load being applied to each bollard it is necessary to recalibrate the load cell periodically. So as to facilitate continuous working of the apparatus the pin 70 (and therefore load cell 24) are replaced with a recently recalibrated pin and the old pin sent away for recalibration. So as to ensure correct and continuous alignment of the pin 70 a notch 76 is cut into the pin and a locking plate 78 is bolted to the shackle 74 so that the locking plate extends into the notch preventing the rotation of the pin. The pin 70 also includes a data feed outlet 80 through which the load data measured by load cell 24 is passed to processor 26 via cable 36.

Further safety and testing elements of the apparatus are the inclusion of acoustic sensors, typically in the form of microphones, for detecting acoustic emissions from within the bollard and the adjacent material. One or more microphones can be provided and these microphones are placed in engagement with the bollard, the ground surface adjacent the bollard or with bollard fixings if they are present (these might include long bolts extending into the concrete forming the quayside). The microphones will detect sound created within the bollard or between the bollard and the concrete of the quayside as the pulling force of the hydraulic ram is applied to the bollard. The processor can be used to interpret these sounds and can be set up so as to identify sounds indicating a problem with the bollard from sounds that are normally produced during the testing of a secure bollard. In the event of the process of detecting a sound which it identifies as being indicating a problem with a bollard, the processor can terminate the test by switching off the hydraulic power pack and releasing the hydraulic ram.

In addition to the acoustic emission testing described above the apparatus can also be provided with sound producing means, in the form of a sending transducer which is located on or adjacent the bollard and transmits a broad band acoustic signal into the bollard and the adjacent material. This signal spreads within the structure and excites half wave resonances and this response of the material provides a characteristic signal which can be used to interpret the integrity of the material. As a result, even before testing is undertaken it is possible to identify damaged bollards. Furthermore, by continuing the transmission of the acoustic signal during the test is possible to identify changes in the signal resulting from changes in the structure. These changes may identify faults in the structure which allows the processor to terminate the test by switching off the hydraulic power pack and releasing the hydraulic ram. As a result of these two tests it is possible to identify damaged bollards at an early stage before the pull test inflicts further damage on the bollard. As a result, it may be possible to repair the bollard and its fixing into the quayside rather than allowing the pull test to inflict further damage which may make repair impossible.

Operation of the apparatus 10 will now be described. To initiate the bollard test, hydraulic ram 22 and load cell 24 are located on trolley 60 between bollards 12 and 14. Hydraulic ram 22 is connected via hydraulic hose 34 to hydraulic power pack 32 and load cell 24 is connected via cable 36 to processor 26. Processor 26 is used to ensure that the hydraulic ram 22 is in a fully extended position, so that it can contract to apply a pulling force. First rope 18 is then attached to load cell 24 and first bollard 12, whilst running over roller 52. In the example shown in FIGS. 1 and 2 the first rope 18 is in the form of a loop and is already attached to load cell 24 allowing it to be simply hooked over bollards 12. Second rope 20, which is attached to the extended hydraulic ram 22, is extended over roller 54, looped around bollard 14 and pulled to take up any slack in ropes 18 and 20. Rope 20 is then looped around the bollard 14 using a suitable knot or other suitably secure tethering technique.

The apparatus 10 is now ready to be used to test the mooring bollards 12 and 14. An operator uses a computer input device (not shown) to instruct processor 26, in particular controller portion 30, to hydraulic power pack 32 to supply or withdrawal hydraulic fluid via hydraulic hose 34 to hydraulic ram 22. As a result, hydraulic ram 22 contracts applying a pulling force via ropes 18 and 22 on bollards 12 and 40. At the same time, data is gathered from load cell 24 into data receiving portion 28 of processor 26 to determine the force that is being applied to the mooring bollards 12 and 40. The test is ideally a non-destructive test and therefore when the data received by processor 26 indicates that the pulling force being applied by hydraulic ram 22 (in other words the tension in ropes 18 and 20) reaches a predetermined level, no further contraction of hydraulic ram 22 takes place. On reaching that predetermined pulling force it can therefore be assumed that the bollards 12 and 14 have passed the test to that standard.

Further data gathering can be used to provide safety cut-outs to the apparatus. For example, cameras 42, 44 and 46 can be used to monitor the first and second bollards and the load cell 24. In the event that the cameras detect movement of the bollards or load cell exceeding a predetermined amount, processor 26 can prevent hydraulic power pack 32 applying more hydraulic fluid transfer tool from hydraulic ram 22 thereby preventing further tension being added to ropes 18 and 20. This can either be in the form of a complete shutdown and release, thereby relieving the tension in ropes 18 and 20 or by reducing the force being applied by ram 22. The data gathered from load cell 24 can also be used to identify potential hazards. For example, a sudden reduction in the tension in load cell 24 may indicate that a bollard has moved. If analysis of this data indicates that the change in tension suggests a movement of the bollards then an immediate shutdown of the apparatus should take place. This data can be analysed alongside the image data from cameras 42 and 44 to provide confirmation. The processor 26 can also be used to distinguish a change in the tension measured by load cell 24 that indicates movement of a bollard compared from other releases of tension within the apparatus such as, for example, the movement of the rope as it initially settles under the tension of initial application of that connects the second rope 22 second bollard 14 which would not require a complete shutdown of the apparatus.

A particularly preferred version of the apparatus includes location recording apparatus, such as a GPS receiver for accurately identifying the location that the testing was undertaken. The GPS receiver can be located on the trolley 60, on the vehicle, on the camera 42 and 44 adjacent the bollard or more than one GPS receiver can be used. By recording the location, taking images of the bollard and recording test data the apparatus is able to record data clearly identifying each bollard that has been tested. As a result, this data can be downloaded and/or transmitted to a central location to create a test certificate clearly and unambiguously identifying the bollard tested and providing data evidencing the test and results. As a result, a single authority can issue bollard compliance certificates based on results produced from to pull different test apparatus.

It will be appreciated by person skilled in the art that the above embodiments have been described by way of example only and not in any limitative sense, and that various alterations and modification are possible without departure from the scope of protection which is defined by the appended claims. For example, the data may be gathered remotely and sent via some suitable wireless data connection to processor 26 which controls hydraulic power pack 32 through a similar wireless data connection. As a result the data cables and hydraulic hose can be shortened whilst maintaining the operator, data input system and processor 26 at a suitable safe distance. Furthermore, the apparatus may be provided with driven wheels or tracks connected to a hydraulic motor which, under the guidance of a remote control connection, can be used to guide the apparatus into position.

The invention claimed is:

1. An apparatus for testing a mooring bollard, the apparatus comprising:
    a first connector for attaching the apparatus to a first bollard;
    a second connector for attaching the apparatus to a second bollard;
    at least one pulling device for applying a pulling force to said first and second bollards via said first and second connectors, said pulling device under the control of at least one controller;
    at least one pulling force measuring device connected between said pulling device and one of said first and second connectors, for measuring the pulling force being applied between the first and second bollards, wherein data from said measuring device is recorded on at least one data logging device; and
    at least one image data capturing device for capturing image data relating to at least one of said first bollard, said second bollard, and said pulling force measuring device, wherein said image data capturing device is connected to said controller such that said controller controls power to said pulling device in response to said image data indicating a movement exceeding a predetermined level.

2. An apparatus according to claim 1, further comprising at least one connector lifter for engaging at least one of said first and second connectors causing it to extend from its attachment to a respective one of said first and second bollards at an angle not parallel to a line connecting said first and second bollards.

3. An apparatus according to claim 2, wherein the connector lifter comprises at least one roller that directly contacts and supports said at least one of said first and second connectors.

4. An apparatus according to claim 1 further comprising an acoustic sensor positioned on or adjacent to at least one of the first and second bollards for detecting acoustic emissions during a test.

5. An apparatus according to claim 4 further comprising a sound generator positioned on or adjacent to the at least one of the first and second bollards for creating acoustic resonance within a material forming and adjacent to the at least one of the first and second bollards.

6. An apparatus according to claim 1, wherein at least one of said first and second connectors comprise ropes.

7. An apparatus according to claim 6, wherein said ropes comprise ultra-high molecular weight polyethylene.

8. An apparatus according to claim 1, wherein said pulling device comprises at least one hydraulic ram.

9. An apparatus according to claim 1, wherein said pulling force measuring device comprises at least one load cell.

10. An apparatus according to claim 1, further comprising at least one processor for processing said data and providing signals to said controller in response to said data.

11. An apparatus according to claim 1, further comprising safety connectors attached to said first and second bollards and configured for attachment to further bollards.

12. The apparatus according to claim 1 wherein the controller causes the pulling device to stop or reduce the pulling force upon the movement of said at least one of said first bollard, said second bollard, and said pulling force measuring device exceeding the predetermined level.

13. A method of testing a mooring bollard, comprising the steps:
attaching a first connector to a first bollard;
attaching a second connector to a second bollard, wherein the first and second connectors are connected to at least one pulling device for applying a pulling force to said first and second bollards via said first and second connectors under the control of at least one controller, and at least one pulling force measuring device connected between said pulling device and one of said first and second connectors, for measuring the pulling force being applied between the first and second bollards;
using said controller to cause said pulling device to apply said pulling force to said first and second bollards via said first and second connectors and recording data generated by said pulling force measuring device on at least one data logging device; and
connecting at least one image data capturing device to said controller, said at least one image data capturing device capturing image data relating to at least one of said first bollard, said second bollard, and said pulling force measuring device, wherein said controller controls power to said pulling device in response to said image data indicating a movement exceeding a predetermined level.

14. A method according to claim 13, further comprising locating at least one connector lifter between at least one of the first and second bollards and said pulling device, the connector lifter for engaging at least one of said first and second connectors causing it to extend from its attachment to a respective one of said first and second bollards at an angle not parallel to a line connecting said first and second bollards.

15. A method according to claim 13, further comprising an acoustic sensor positioned on or adjacent to at least one of the first and second bollards for detecting acoustic emissions on or adjacent to the one of the first and second bollards during said test.

16. A method according to claim 15 further comprising a sound generator positioned on or adjacent to the one of the first and second bollards for creating acoustic resonance within the material forming and adjacent the one of the first and second bollards.

17. A method according to claim 13, further comprising using at least one processor to process said data and provide signals to said controller in response to said data.

18. A method according to claim 13, further comprising analysing said data and determining whether said data indicates a pass or fail.

19. The method according to claim 13 wherein said controller causes the pulling device to stop or reduce the pulling force upon the movement of said at least one of said first bollard, said second bollard, and said pulling force measuring device exceeding the predetermined level.

20. An apparatus for testing a mooring bollard, the apparatus comprising:
a first connector for attaching the apparatus to a first bollard;
a second connector for attaching the apparatus to a second bollard;
a pulling device located between and coupled to said first and second connectors for applying a pulling force to said first and second bollards via said first and second connectors;
a first connector lifter located between said pulling device and said first bollard and engaging said first connector, wherein a first portion of the first connector extends from the pulling device to the first connector lifter and a second portion of the first connector extends downwardly relative to the first portion of the first connector from the first connector lifter to the first bollard;
a second connector lifter located between said at least one pulling device and said second bollard and engaging said second connector, a first portion of the second connector extending from the pulling device to the second connector lifter and a second portion of the second connector extending downwardly relative to the first portion of the second connector from the second connector lifter to the second bollard;
at least one pulling force measuring device connected between said pulling device and one of said first and second connectors for measuring the pulling force being applied between the first and second bollards; and
a processor comprising a controller and a data logging device, wherein the controller is operably coupled to the at least one pulling device to control operation of the at least one pulling device, and wherein the pulling force measuring device is operably coupled to the data logging device to transmit data from said pulling force measuring device to said data logging device.

* * * * *